United States Patent [19]

Capomacchia et al.

[11] Patent Number: 5,434,085
[45] Date of Patent: Jul. 18, 1995

[54] METHOD AND APPARATUS FOR SUPEROXIDE AND NITRIC OXIDE MEASUREMENT

[75] Inventors: Tony Capomacchia, Stone Mountain; Ngoc H. Do, Athens, both of Ga.

[73] Assignee: University of Georgia Research Foundation, Inc., Athens, Ga.

[21] Appl. No.: 207,390

[22] Filed: Mar. 8, 1994

[51] Int. Cl.$^6$ .................. G01N 21/31; G01N 21/64; G01N 33/52
[52] U.S. Cl. .................. 436/116; 436/136; 436/172; 422/82.06; 422/82.08; 356/73.1
[58] Field of Search .................. 252/582, 600, 700; 436/116, 136, 172, 135; 422/52, 81, 82.05, 82.06, 82.08; 356/73.1

[56] References Cited

U.S. PATENT DOCUMENTS

| | | | |
|---|---|---|---|
| 3,659,100 | 4/1972 | Anderson et al. | 250/71 R |
| 5,238,610 | 8/1993 | Thompson | 252/700 |
| 5,252,494 | 10/1993 | Walt | 436/528 |
| 5,322,799 | 6/1994 | Miller et al. | 436/165 |

OTHER PUBLICATIONS

Greenlee, L. et al. (1962), "Chemiluminescence Induced by Operation of Iron-Flavoproteins," *Biochemistry* 1:779-783.
Huu, T. P. et al. (1984), "Luminol Assay for Microdetermination of Superoxide Dismutase Activity: Its Application to Human Fetal Blood," *Anal. Biochem.* 142:467-472.
Corbisier, P. et al. (1987), "A New Technique for Highly Sensitive Detection of Superoxide Dismutase Activity by Chemiluminescence," *Anal. Biochem.* 164:240-247.
Pascual, C. et al. (1992), "A New Luminol Sensitized Chemiluminescence Method for Determination of Superoxide Dismutase," *Anal. Lett.* 25:837-849.
Peters, T. R. et al. (1990), "Lucigenin Chemiluminescence as a Probe for Mesuring Reactive Oxygen Species Production in *Escherichia coli*," *Anal. Biochem.* 186:316-319.
Archer et al. (1989), "Simultaneous Measurement of $O_2$ Radicals and Pulmonary Vascular Reactivity in Rat Lung," *J. Appl. Physiol.* 67:1903-1911.
Archer et al. (1989), "Detection of Activated $O_2$ Species In Vitro and in Rat Lungs by Chemiluminescence," *J. Appl. Physiol.* and 1912-1921.
Henry et al. (1990), "Enhanced Chemiluminescence as a Measure of Oxygen-Derived Free Radical Generation During Ischemia and Reperfusion," *Circulation Res.* 67:1453-1461.
Gyllenhammar (1987), "Lucigenin Chemiluminescence in the Assessment of Neutrophil Superoxide Production," *J. Immunol. Meth.* 97:209-213.
Zafiriou, O. P. et al. (1980), "Determination of Trace Levels of Nitric Oxide in Aqueous Solution," *Anal. Chem.* 52:1662-1667.
Kikuchi, K. et al. (1993), "Detection of Nitric Oxide Production from a Perfused Organ by a Luminol—$H_2O_2$ System," *Anal. Chem.* 65:1794-1799.
Radi, R. et al. (1993), "Peroxynitrite-induced Luminol Chemiluminescence," *Biochem. J.* 290:51-57.
Saran and Bors (1991), "Direct and Indirect Measurements of Oxygen Radicals," *Klin. Wochenschrift* 69:957-964.

Primary Examiner—David A. Redding
Attorney, Agent, or Firm—Greenlee and Winner

[57] ABSTRACT

A method of assaying superoxide ($O_2^-$) or nitric oxide (NO) in an aqueous sample includes an initial step of trapping $O_2^-$ or NO in an emulsion or micellar suspension of a trapping solvent, then reacting the trapped analyte with an appropriate analytical reagent. A flow apparatus for carrying out the method is disclosed. Specific reaction conditions for using chemiluminescence to measure the analytes are also disclosed.

15 Claims, 5 Drawing Sheets

METHOD AND APPARATUS FOR SUPEROXIDE AND NITRIC OXIDE MEASUREMENT

FIELD OF THE INVENTION

The invention relates the measurement of superoxide ($O_2^-$) and/or nitric oxide (NO) in solution, especially as these substances are generated in an aqueous environment. The disclosed apparatus and method are adopted to measurement of $O_2^-$ and/or NO found in biological materials, including tissue samples.

BACKGROUND

Superoxide ($O_2^-$) is an anionic, one-electron reduced form of molecular oxygen. For a review of the chemistry of superoxide, see Sawyer, D. T., et al. (1981) *Acc. Chem. Res.* 14:393–400. Following Sawyer, et al., the symbol $O_2^-$ is used herein to denote superoxide. Superoxide is very reactive in aqueous solutions and protic solvents. The rate constant for $O_2^-$ reaction with $H_2O$ is $\approx 1 \times 10^7$/mol/sec (Sawyer, et al., 1981). On the other hand, $O_2^-$ is quite stable in aprotic solvents. In general $O_2^-$ behaves as an oxidant, and as a strong nucleophile, depending on the solvent, in particular on the pH or presence of an easily abstractable hydrogen atom. Superoxide also acts as a one-electron reductant of metal ions and complexes.

Superoxide is generated in biological systems as a consequence of aerobic respiration. It is now widely accepted that $O_2^-$ is an important agent in the toxicity of oxygen. All oxygen-metabolizing cells so far examined have been found to contain an enzyme activity, termed superoxide dismutase (SOD) which catalyzes the reaction: $O_2^- + O_2^- + 2H^+ \rightarrow H_2O_2 + O_2$.

The superoxide dismutases are considered to play a major role in protecting cells and tissues against $O_2^-$. Recently, the genetic defect of ALS (amyelotropic lateral sclerosis), or Lou Gehrig's Disease, has been determined to be a defective SOD which leads to progressive peripheral nerve degeneration. For a review of SOD, see Fridovich, I. (1974) *Adv. Enzymol.* 41:35–97. Other neuro-degenerative disorders have been linked to oxidative stress involving, at least in part, $O_2^-$ [Coyle, J. T. et al. (1993) *Science* 262:689–695]. Superoxide has also been implicated in tissue inflammatory reactions, and in myocardial tissue damage following the clearing of an infarcted vessel with streptokinase or plasminogen activator. Certain oxidative enzymes, e.g., xanthine oxidase, are known to generate $O_2^-$ in the course of oxidizing substrate. The $O_2^-$ generated by action of xanthine oxidase catalyzing an oxidation of a substrate has been measured by a chemiluminescence reaction, Greenlee, L., et al. (1962) *Biochemistry* 1:779–783. The reaction was shown to activate the chemiluminescence of luminol (5-amino-2,3-dihydro-1,4-phthalazinedione) or lucigenin (dimethylbiacridylium) at pH 10.0.

The activity of SOD has been measured by chemiluminescence, using xanthine oxidase to generate $O_2^-$ measured by chemiluminescent light intensity, which is inhibited by the activity of SOD. Huu, T. P., et al. (1984) *Anal. Biochem.* 142:467–475 reported a SOD assay using luminol luminescence and $O_2^-$ generated by xanthine oxidase. A steady state of light intensity was obtained when both xanthine oxidase and SOD were present, the level being dependent on SOD activity when xanthine oxidase was constant. Corbisier, P., et al. (1987) *Anal. Biochem.* 164:240–247 reported an assay for SOD based on chemiluminescence of lucigenin, using the xanthine oxidase system to generate $O_2^-$. Pascual, C., et al. (1992) *Anal. Lett.* 25:837–849 reported an SOD assay using luminol, hydrogen peroxide ($H_2O_2$) and horseradish peroxidase (HRP), in which the action of the peroxidase on luminol was reported to generate $O_2^-$ which activated luminol chemiluminescence, which was inhibited by SOD. However, the reaction of lucigenin has been reported to be specific for $O_2^-$ whereas luminol chemiluminescence is induced by a variety of agents [Peters, T. R., et al. (1990) *Anal. Biochem.* 186:316].

Direct measurement of $O_2^-$ has been difficult because of its short lifetime in aqueous solution, and also because of its reactivity with $H_2O$ and $H_2O_2$ to generate free radical chain reactions which are difficult to quantify with chemiluminescence. Consequently, it has not heretofore been possible to measure $O_2^-$ satisfactorily in aqueous samples, especially in biological materials. [Saran and Bors (1991) *Klin. Wochenschrift* 69:957–964].

Published methods for measuring $O_2^-$ include direct measurement using electron spin resonance (ESR) and indirect measurement using chemiluminescence or dye reduction. ESR measurement of $O_2^-$ has been disclosed, for example, by Aust, et al. (1993) *Toxicol. Appl. Pharmacol.* 120:168–178; Samuni et al. (1988) *Free Radical Biol. Med.* 6:141–148; and Buettner (1990) *Free Rad. Res. Comm.* 10:11–15. Chemiluminescence measurement using luminol or lucigenin has been disclosed by Archer, et al. (1989) *J. Appl. Physiol.* 67:1903–1911 and 1912–1921; Henry, et al. (1990) *Circulation Res.* 67:1453–1461) and Gyllenhammar (1987) *J. Immunol. Meth.* 97:209–213. Dye reduction methods include reduction of cytochrome c [Fridovich, I., in *CRC Handbook of Methods for Oxygen Radical Research* (Greenwald, R. A., ed.) pp. 121–122]; reduction tetranitromethane [Bielski, et al. (1985) *J. Phys. Chem. Ref. Data* 14:1041–1091 and nitro blue tetrazolium (Auclair and Voisin in *CRC Handbook*, pp. 123–132). ESR measurements are qualitative rather than quantitative due to the nonspecific nature of the interaction of $O_2^-$ with the spin-trapping agents used in these studies. As noted, $O_2^-$ is unstable in aqueous milieu, a factor which has limited the sensitivity of both chemiluminescent and dye reduction methods. The latter are further limited by the relatively low sensitivity of absorbance measurements in the visible spectrum. In addition, other oxidizing or reducing agents present in the sample can reduce the accuracy of the results, and further degrade sensitivity.

Nitric oxide (NO) has recently been shown to act as a short-range cell signal transmitter. For example, NO has been shown to act in vascular endothelium as the endothelium-derived relaxing factor (EDRF), and therefore to be an important component of blood pressure regulation. NO has also been shown to function in the causation of erection in male rats. In addition, NO acts as a signal transmitter in both central and peripheral neurons [Garthwaite, J. (1988) *Nature* 336:385–388; Radomski, M. W., et al. (1987) *J. Pharmacol.* 92:639–644]. For a review of NO physiological activities, see *Nitric Oxide from L-Arginine: A Bioregulatory System* (Moncada, S. and Higgs, E. A. eds) Elsevier, Amsterdam 1990.

Various chemiluminescent reactions have been used to measure NO. Anderson, et al., U.S. Pat. No. 3,659,100 disclosed a method for monitoring air pollutants, including NO. Air containing NO is passed through an adsorption column to remove interfering pollutants, then passed through a limiting orifice where a luminol-$H_2O$ solution is dispersed as droplets in the gas stream. Luminescence occurs on the surface of the droplets and measured by a photocell. A common method of measuring NO in the gas phase also involves chemiluminescence, but does not employ luminol. Sample gas is mixed with ozone which reacts with NO to yield an activated $NO_2$ which yields a red chemiluminescence which can be measured by a photon counting system. The method has been adapted to measure NO in aqueous samples by Zafiriou, O. P., et al. (1980) Anal. Chem. 52:1662–1667. The procedure involved stripping the NO from an aqueous solution by flowing a gas stream through the solution, and then measuring NO in the gas phase using the conventional ozone-$NO_2$ chemiluminescent system. Yet another assay for NO in aqueous medium was described by Mordvintcev, P., et al. (1991) Anal. Biochem. 199:142–146. The authors reacted NO with $Fe^{2+}$-DETC (diethyldithiocarbamate) to form a NO-$Fe^{2+}$-DETC complex. The complex was paramagnetic, allowing detection by electron paramagnetic resonance spectroscopy. Kikuchi, K., et al. (1993) Anal. Chem. 65:1794–1799, reported a chemiluminescent reaction to detect NO, using $H_2O_2$ and luminol at neutral pH. $H_2O_2$ was reported to react with NO to yield peroxynitrite ($ONOO^-$) which was said to be the reactant which initiated luminol chemiluminescence. The reported limit of detection was 100 fM, and NO detection in the picomolar range from a perfused rat kidney was described. Interfering luminescence of luminol caused by the presence of hemoglobin and $H_2O_2$ was removed by adding desferrioxamine at an optimized concentration. Radi, R., et al. (1993) Biochem J. 290:51–57 reported further characteristics of peroxynitrite-induced luminol chemiluminescence in a nonbiological system using a quenched flow peroxynitrite generating system. The effect of $O_2^-$ in the system was studied by adding potassium superoxide. Peroxynitrite alone was able to induce chemiluminescence of luminol. Both $O_2^-$ and bicarbonate enhanced chemiluminescence suggesting a complex interplay of intermediate reactants affecting the quantitative results. Neither NO nor $O_2^-$ alone were capable of directly inducing significant luminol chemiluminescence.

Other NO assays include trapping of NO by nitroso compounds or nitronyl nitroxides [Joseph, et al. (1993) Biochem. Biophys. Res. Comm. 192:926–934], or by reduced hemoglobin to form an adduct detectable by ESR. Measurement of hemoglobin reduced to Inethemoglobin by NO can be detected spectrophotometrically. A carbon fiber amperometric sensor using metal-porphyrin dispersed in an amorphous silica matrix has been reported [Malinsk et al. (1992) Nature 358:676–678]. Also, an NO sensor using aquocyanobinamide in a silica microprobe has been used to measure NO from tissues and single cells [Shibuki (1990) Neurosci. Res. 9:69–70).

ESR (also called electron paramagnetic resonance) suffers from low and variable spin-trapping efficiency, relatively high cost and many artifacts that hinder analysis [Greenberg et al. (1990) Circ. Res. 67:1446–1452]. The spectrophotometric methods are nonspecific and subject to redox cycling, as in the cytochrome c assay for $O_2^-$ [Archer (1993) Faseb J. 7:349–360]. The ozone assay for NO is reportedly quite specific, however, there are several potential problems caused by acidification of samples and strong reducing conditions prior to measurement [Archer (1993); Chung et al. (1990) J. Pharmacol. Exp. The. 253:614–619]. The use of acids or reducing agents will enhance the chemiluminescence signal, but will tend to cause overestimation of NO levels. In the absence of acids or reducing agents a 10-fold decreased signal can be experienced. There is also potential for oxygen reaction with NO to form nitrates and nitrites. A further disadvantage of the NO/ozone assay is that the equipment for carrying out the assay is relatively costly.

The quantitative assay of $O_2^-$ and NO in aqueous media, especially biological materials, has been extremely difficult to achieve satisfactorily because the extreme lability and reactivity of these compounds and because they are present in minuscule amounts in samples of interest. Chemiluminescence has potential to provide the requisite sensitivity but loss of analyte due to lability and/or side reactions remains an unsolved problem. When NO or $O_2^-$ is generated by a tissue, for example, the true amount present in the tissue remains unknown, since most analyte is believed lost in transit to the cell where the analytical reaction occurs.

SUMMARY OF THE INVENTION

The present invention overcomes the problems heretofore encountered in the art by trapping $O_2^-$ or NO in situ in a nonaqueous, aprotic solvent present dispersed as an oil-in-water emulsion or as micelles, in which the $O_2^-$ or NO are both readily soluble and highly stable. The trapping mixture is then reacted with an analytical reagent capable of reacting with $O_2^-$ or NO to give a measurable signal proportional to the concentration of trapped $O_2^-$ or NO. In a preferred embodiment the analytical reagent is a chemiluminescent reagent which yields light upon reaction with $O_2^-$ or NO. Chemiluminescent light is measured by conventional photomultiplier and photon counting equipment. Superoxide can be measured independently by using lucigenin as chemiluminescent reagent, since the reagent is specifically activated by $O_2^-$. NO is assayed using luminol in the presence of $H_2O_2$, which oxidizes NO to $ONOO^-$ which activates luminol luminescence.

The invention also provides a unique sampling probe that provides for direct sampling of fluid flowing over a tissue surface and immediate trapping in an emulsion or micellar suspension, while avoiding direct contact of the tissue by the trapping solvent. The probe allows $O_2^-$ and NO to be immediately trapped as they are washed from the cell surfaces of a tissue sample.

The invention further provides an analytical apparatus which provides continuous sampling of tissue, trapping of $O_2^-$ and NO, direct flow to a reaction cell, continuous introduction of analytical reagent and continuous read-out of the analytical reaction signal, e.g., chemiluminescence intensity. Different embodiments of the apparatus are described herein for specific assay of $O_2^-$ or of NO or both, as desired.

DETAILED DESCRIPTION OF THE INVENTION

Figure 1:
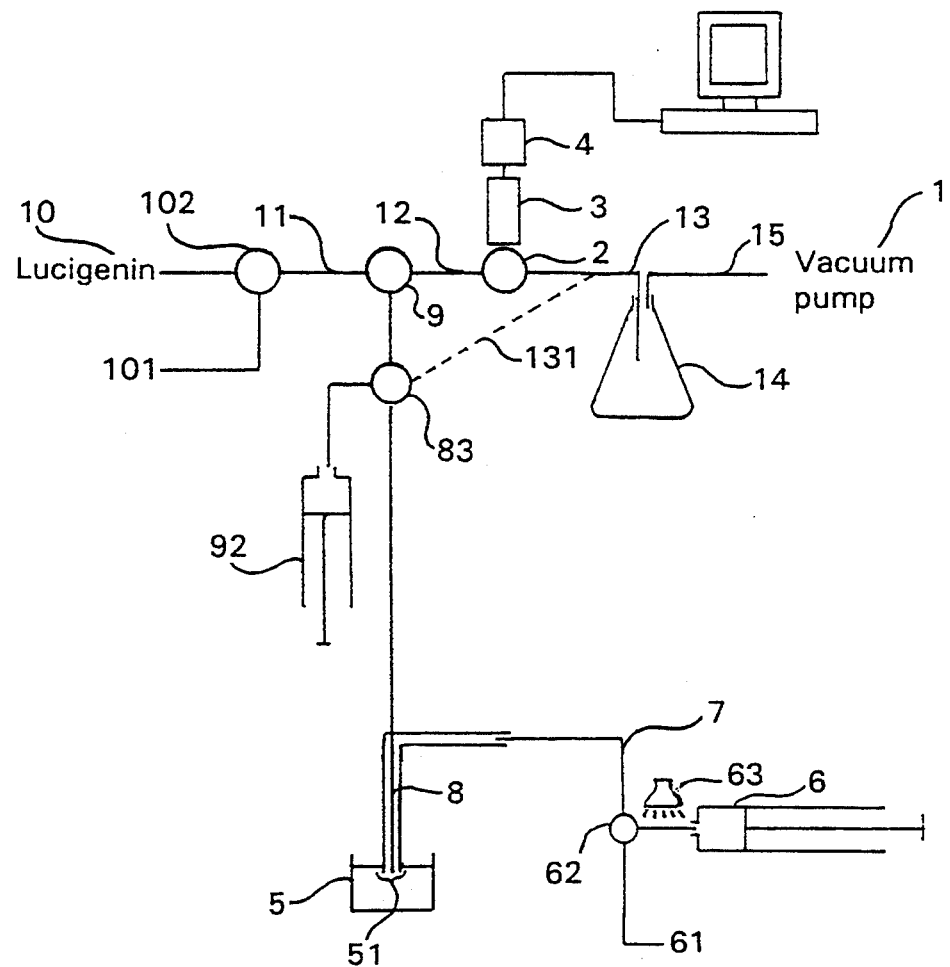
FIG. 1 is a diagrammatic representation of an apparatus for measuring $O_2^-$ or NO or both, showing the flow pathways of sample, trapping mixture, and reagents.

The present invention is an assay method for measuring $O_2^-$ and/or NO present in an aqueous medium such as a sample of biological material. The method avoids the significant decay of $O_2^-$ and NO in aqueous media by trapping these analytes in an aprotic solvent, where they can be stable for hours. For example, in one test, $O_2^-$ trapped in an oil-in-water emulsion of octane was stable for three hours. The aprotic solvent trapping agent is dispersed in an aqueous carrier, for example as an oil-in-water emulsion, or preferably as a micellar suspension. Any nonpolar aprotic solvent which can form an emulsion or micellar suspension can serve as a trapping agent. Octane is a preferred nonpolar solvent because it has formed the most stable emulsions among the solvents tested. The aprotic solvent is $O_2$-free, in order to prevent loss of NO or $O_2^-$ by reaction with oxygen. In practice, the solvent can be rendered $O_2$-free by equilibration with a gas stream of pure $N_2$. Cationic surfactants can be used to stabilize emulsions, or to form micellar systems. The latter are preferred because they appear to trap $O_2^-$ and NO more efficiently than emulsified octane. A preferred micellar system is formed by dissolving the surfactant cetyl trimethylammonium bromide (CTAB) in isopropanol, then dissolving this solution in octane. The clear solution so formed contains micelles of CTAB in which the polar ammonium groups are believed to be oriented inwardly and solvated by the isopropanol. The nonpolar hexadecyl tails of the CTAB molecule are thought to be oriented outward and are readily solvated by the octane. While the invention is not limited by any specific theory of operation, it has been observed that the micellar system is more efficient than emulsion trapping, presumably because $O_2^-$; NO or $ONOO^-$ produced by oxidation of NO are more readily partitioned into the octane solution containing the micelles than in the outer aqueous layer of an oil-in-water emulsion.

The trapping mixture just described permits the assay of $O_2^-$ or NO by any means compatible with the materials employed. Once $O_2^-$ and NO have been removed from the aqueous environment where they are highly labile, any measurement system having the desired sensitivity and specificity can be used as part of the invention. The quantity of the response measured must be a function of the amount of $O_2^-$ or NO in the sample being assayed. Chemiluminescence is an attractive measurement system because of the high sensitivity of currently available light measurement devices, and because the reactivity of known chemiluminescent reagents can be controlled to provide the requisite specificity. The invention is not to be construed as limited to chemiluminescence since other measurement techniques, both direct and indirect, can be applied to measure trapped $O_2^-$ or NO. Such techniques include but are not limited to ESR, amperometric measurement using a gas permeable membrane probe, or the ozone reaction with NO, measuring ozone luminescence.

Turning now to FIG. 1, the operation of an apparatus employing the above-described trapping system is described, for measuring $O_2^-$ or NO by a chemiluminescent reaction. The apparatus provides for measurement to be carried out in a continuous flow manner, with net flow being provided by vacuum pump 1. The chemiluminescence is measured by conventional means such as one used in HPLC luminescence detectors. The components are a flow cell 2, often comprising a coil of teflon tubing, a photomultiplier tube 3, a photon counter 4 and data analysis means such as a computer and appropriate software. Sample 5 containing analyte is drawn into the inner micropipette 8 toward the mixing cell 9. The orifice of the inner micropipette 8 is contained within the sample probe 51 which is shown in detail in FIG. 2. A trapping mixture pump 6, show diagrammatically as a syringe, drives preformed trapping mixture, either emulsion or micellar system toward the sample probe 51 via the outer micropipette 7. Optionally, a second pumping system 61 is used to drive a separate trapping mixture containing $H_2O_2$ for NO measurement through outer micropipette 7 to the sample probe 51. A three-way valve 62 is provided to allow the operator to select between pumps 6 and pump 61. For NO measurement, an optional UV light source 63 is positioned to irradiate the trapping mixture. Both sample and emulsion flow from sample probe 51 through inner micropipette 8 toward mixing cell 9, where mixing with the chemiluminescent reagent occurs. For $O_2^-$ assay, reagent pump 10 pumps a hydroalcoholic solution of lucigenin through tubing 11 toward mixing cell 9. Optionally, a second reagent pump 101 is connected to tubing 11 via a three-way valve 102. Reagent pump 101 pumps luminol through tubing 11 to mixing cell 9, for measuring NO in the sample. Mixing cell 9 is connected directly or through tubing 12 to the coil teflon flow cell 2 where the intensity of the light reaction is measured, as previously described. Optionally, a fixed volume loop sample injector 83, also termed an HPLC injector, is provided to provide precise control of sample passed through the flow cell 2. The sample injector 83 acts to fill a loop of tubing with a fixed volume of sample from the sample probe 51. The injector 83 is then switched to deliver the fixed volume of sample to the mixing cell 9, during which time sample flow from probe 51 is shunted to waste via bypass tubing 131. A syringe pump 92 is employed to propel the fixed sample volume contained in the tubing loop of injector 83 toward mixing cell 9. Spent reagent and reactants exit the flow cell 2 via tubing 13 toward waste trap 14 or other collecting means, in the vacuum line 15. The flow rates of the vacuum pump 1, trapping mixture pumps 6 or 61 and reagent pumps 10 or 101 are regulated such that net flow in outer micropipette 7 is toward sample probe 51, flow in inner micropipette 8 and in tube 11 is toward mixing cell 9 and flow in tube 12 and 13 is toward waste trap 14.

Figure 2:
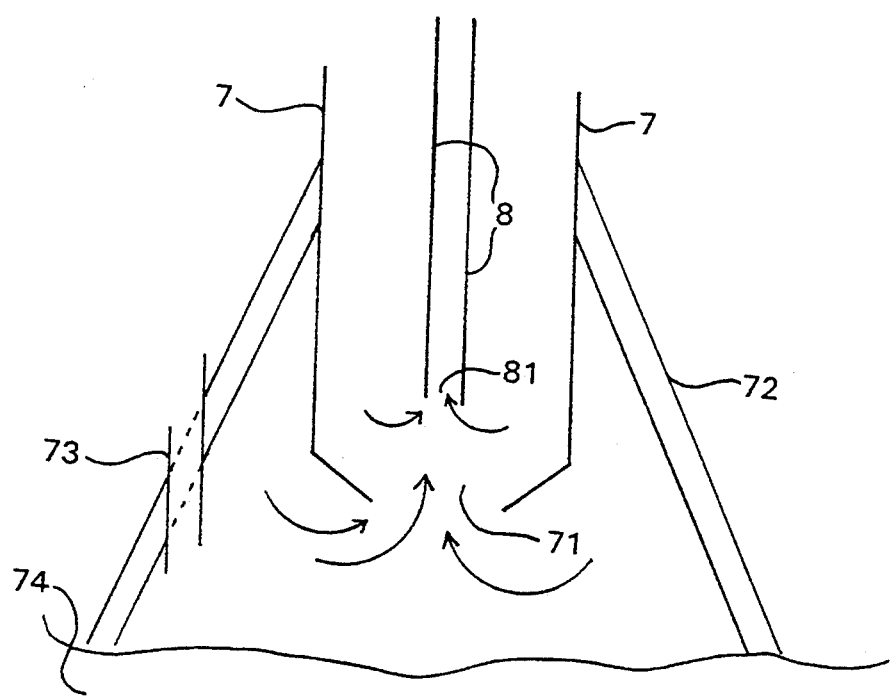
FIG. 2 is a diagram of a sampling probe shown in cross section. The sampling probe is designed to provide immediate trapping of $O_2^-$ and NO emanating from a tissue surface.

Details of sample probe 51 are shown in FIG. 2. The walls of outer micropipette 7 and inner micropipette 8 are shown disposed as concentric cylinders. The opening 71 of outer micropipette 7 is extended beyond the opening 81 of inner micropipette 8. However, opening 71 is prevented from touching the surface of tissue sample 74 by spacer means 72 which are dimensioned to extend slightly beyond opening 71 to permit fluid flow, shown by arrows, across the surface of tissue sample 74 and into opening 71. Spacer means 72 can be any sort of mechanical spacer such as legs or a skirt as long as means such as slot 73 are provided to permit fluid flow around and through spacer means 72 into opening 71. The opening 81 of inner micropipette 8 is slightly recessed relative to opening 71 and tissue sample 74. Sample fluid containing $O_2^-$ or NO flowing over tissue sample 74 is drawn upward through opening 71, where the sample encounters trapping mixture flowing downward through outer micropipette 7. Sample fluid and trapping mixture mix and flow together upwardly through orifice 81 and through inner micropipette 8. In operating the apparatus, the rate of flow of trapping mixture through outer pipette 7 is such that no trapping mixture fluid exits opening 71, in order to prevent trapping mixture solvent from contacting tissue sample 74.

Figure 3:
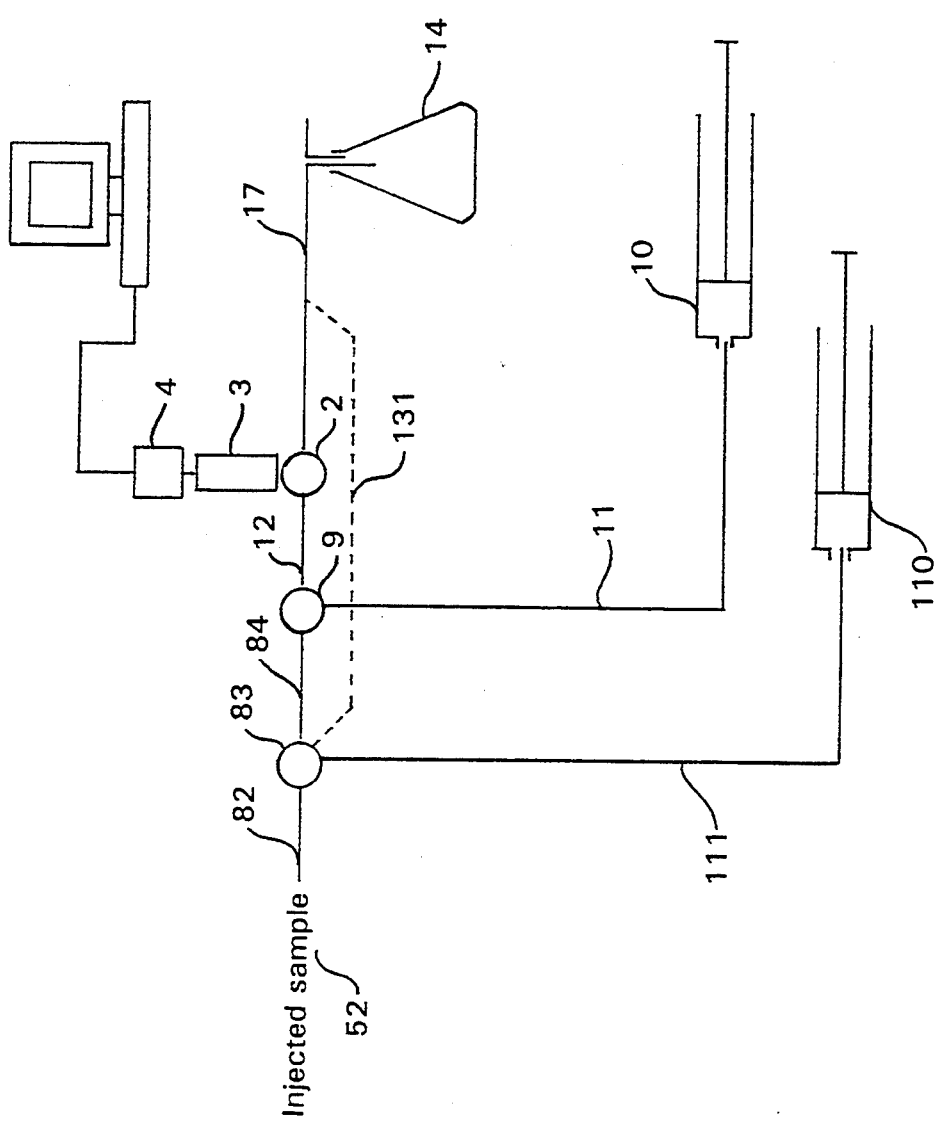
FIG. 3 is a diagrammatic representation of a variant of the $O_2^-$ measuring apparatus, specifically adapted for measuring $O_2^-$ trapped in cells, such as erythrocytes, rather than in micelles or emulsion droplets.

FIG. 3 depicts a modification of the device of FIG. 1, used for assaying a sample comprising $O_2^-$ or NO in trapped form. In the use of this embodiment of the device the trapped form may be particles of emulsion, micellar system, or, as further described below, individual cells. In either case, the sample is contacted with chemiluminescent reagent in medium which disrupts the trapped state and permits chemical contact between the reagent and the analyte. A sample pumping means 52 pumps a sample of trapped analyte through tubing 82 to an injector fixed volume loop sample 83, also termed an HPLC injector. Buffer supplied through tube 111 by syringe pumping means 110 propels sample from the injector toward mixing cell 9. At the same time, sample is shunted to waste via tube 131. Chemiluminescence reagent in media capable of disrupting the trapped state is delivered by pumping means 10 through tube 11 to mixing cell 9 where the reagent is mixed with sample delivered through tube 84 from injector 83. The mixture then passes from the mixing cell 9 through tube 12 to coiled teflon flow cell 2 where chemiluminescence is measured as previously described. Fluid exiting flow cell 2 passes through tube 17 to waste trap 14. The pumping rates of pumps 52, 10, and 110 are adjusted to provide for fluid flow from pumps 52 and 110 to HPLC injector 83, from pump 10 toward mixing cell 9, from HPLC injector 83 to mixing cell 9 and from mixing cell 9 in the direction of flow cell 2 and waste trap 14.

It can be seen that the apparatus of the invention embodies several features which can be accomplished by a variety of expedients. The sample probe, for example, can be any sort of means for drawing a sample of fluid to be analyzed into the apparatus, such as syringe needle or micropipette. Preferably, the sample probe is adapted to provide rapid mixing between the fluid to be analyzed and the trapping mixture, as promptly as possible after the sample enters the probe. A mixing cell is any volume where mixing can occur between two fluid streams, for example, trapped sample and the analytical reagent. The mixing cell may simply be placed when the two streams merge, although provision for rapid mixing should be made, to prevent laminar flow or gradual mixing to occur. Mixing can be accomplished by shaping the mixing cell to cause turbulence, by directing the two streams towards each other, by imposing mechanical or vibratory motions, and the like. A detection cell is any part of the apparatus downstream of the mixing cell, which permits the reaction signal to be detected. The nature of the reaction signal dictates the nature of the detection cell, as is understood in the art. In the case of chemiluminescence, the material of the detection cell should transmit sufficient light to permit most of the emitted light to be detected. The sample probe, mixing cell and detection cell are connected by fluid flow conducting means, which may be tubing of any inert (to the components of the assay) material, such as teflon capillary tubing. Although the drawings suggest a length of tubing connecting each component, the apparatus can have a design that is more compact, for example, by positioning the various components in contact with one another, in which case the fluid conducting means is simply a port or channel through which fluid passes without loss from one component to the next.

The apparatus also includes means for producing flow of sample, trapping mixture, and analytical reagent through the system. Trapping mixture pumping means can be any means for causing a flow of trapping mixture into the sample, as the latter is drawn into the apparatus. Such means include, but are not limited to, syringe pumps, metering pumps, mechanical pumps or even gravity flow devices. Similarly, the analytical reagent pumping means can be any means for causing a flow of analytical reagent into the sample downstream of the site of trapping mixture introduction, and upstream of, or at, the mixing cell. Such means include, but are not limited to, syringe pumps metering pumps, mechanical pumps, or gravity flow devices. Net flow of fluid through the system is accomplished by net flow generating means, which functions to ensure that the flow of fluid is unidirectional, from the sample probe through the detector cell. Separate pumps for trapping mixture and analytical reagent are preferred, in order to exert positive control of their rates of addition. However, the net flow generating means can be used to generate flow of all fluids (sample, trapping mixture and analytical reagent), the flow rates of each being controlled by passive devices such as metering valves, tubing restrictions or the like. Although depicted in the figures in a position downstream of the detector cell, the net flow generating means can in principle be positioned anywhere within the apparatus. The net flow generating means can be any pumping device capable of creating unidirectional continuous or pulsed flow at the rates appropriate to the apparatus capacity. Preferred pumps are those having fine control capability such as a vacuum/pressure pump model 01-094-22, manufactured by Gast Mfg., available from Fisher Scientific, Atlanta, Ga., or syringe pump model 55-4153 available from Harvard Apparatus, Boston, Mass.

Choice of detection means depends upon the type of signal to be measured. For example, a fluorescence signal would require a fluorometer, an absorbance change would be detectable by a spectrophotometer, and amperometric detection would require a membrane probe, as is well known in the art. In the preferred embodiment, a chemiluminescent signal is detectable by a photometer, photomultiplier tube or photon counter. A standard chemiluminescence detector commercially available for high performance liquid chromatography (HPLC) such as Shodex CL-2, manufactured by Showa Denko America, Inc., New York, N.Y., and available from J.M. Science, Buffalo, N.Y., is a suitable detection means for the apparatus.

In operation, sample flows into the sample probe and is moved through the fluid flow conducting means toward the mixing cell. A flow of trapping mixture is mixed with the sample, preferably as soon after, or simultaneously with, entry of sample into the probe. By the time sample and trapping mixture reach the mixing cell, any $O_2^-$ or NO present in the sample is trapped in the aprotic solvent present as an emulsion or in the micellar phase. A flow of analytical reagent is then introduced to the trapped sample, mixing therewith in the mixing cell. The combined fluids then flow into the detector cell where the reaction signal, e.g., chemiluminescence, is measured. The combined fluids then exit the apparatus, preferably into a waste trap.

A preferred embodiment of the apparatus provides a specialized sample probe, designed to provide immediate trapping of $O_2^-$ or NO, as the sample is drawn into the apparatus. In this embodiment the sample probe includes coaxial micropipettes, an outer micropipette for supplying a flow of the trapping mixture and an inner micropipette for conducting sample and trapping mixture together toward the mixing cell. The opening of the inner micropipette is recessed slightly relative to the opening of the outer micropipette. In operation, the rate of uptake of sample and trapping mixture into the inner micropipette exceeds the rate of flow of trapping mixture in the outer micropipette so that any trapping mixture exiting the outer micropipette is swept into the inner micropipette along with sample. Rapid mixing of sample and trapping mixture is accomplished, while the residence time of emulsion particles or micelles is minimized in the space between the openings of the outer and inner micropipettes. Spacer means, such as stalks, legs or a perforated glass ring, are provided to prevent the opening of the outer micropipette from contacting the surface of the sample area, which can be a live tissue surface. Tissue damage, possibly caused by contact with a component of the trapping mixture, is thereby avoided.

Variations of the apparatus to accommodate specific goals or to analyze specific sample types are readily accomplished by those skilled in the art. For example, since $O_2^-$ and NO analysis requires different trapping mixtures and analytical reagents, the basic apparatus can be adapted to measure either analyte, simply by providing dual reservoirs of trapping mixtures and analytical reagents, and three-way valves to allow switching from one to another. In this variation, the same sample can be rapidly analyzed for both $O_2^-$ and NO. Similarly, analysis of $O_2^-$ or NO biologically trapped in whole cells can be carried out in a variant of the apparatus lacking a trapping mixture pump. In yet another variation, a trapping mixture such as an emulsion can be generated in situ, by pumping two components of the mixture together prior to contacting the sample.

The preferred trapping mixture for trapping $O_2^-$ or NO is a micellar system in which a cationic detergent such as CTAB is first dissolved in isopropanol, then the solution is dissolved in octane. For $O_2^-$ analysis, 50 mg CTAB is dissolved in 4 ml isopropanol, then in 7 ml of octane. The order of mixing is important since CTAB does not dissolve directly in octane unless first dissolved in isopropanol. For NO analysis, 1 ml CTAB is dissolved in 1 ml isopropanol which is then dissolved in 10 ml octane. The resulting micellar mixture appears clear and has been found to be highly efficient for trapping both $O_2^-$ and NO. The trapped $O_2^-$ is not stable for as long a period of time as $O_2^-$ trapped in an octane emulsion. However, the stability of micelle trapped $O_2^-$ is on the order of several minutes, which is more than adequate for the present method, since only a few seconds, at most, are required for the trapped $O_2^-$ to flow from sample to detector. At the point where mixing of the trapping mixture and sample occurs, trapping efficiency is maximized if the surface area of the trapping mixture in contact with sample is maximized. Various techniques known in the art can be used to maximize the surface area of the trapping mixture, the preferred means being to provide for turbulence at the point of mixing. Other means, such as ultrasonic vibration and mechanically dispersing the trapping mixture by the use of a frit or screen are well-known to those skilled in the art.

An oil-in-water emulsion trapping mixture can be employed, for example using a 1:3 ratio (v/v) of octane and commercially-available Krebs-Hensleit buffer solution stabilized by cationic detergent, for example CTAB in the range 0.005M–0.2M in Krebs-Hensleit buffer. The emulsion can be formed by any known method, for example by vortex mixing, sonication and the like. An emulsion can also be formed in situ by pumping two opposing streams of buffer and octane into the outer micropipette 7 of FIG. 1. Preformed emulsion is stable for several hours, however, and is therefore preferred.

The same emulsion and micellar trapping mixtures can be used for either $O_2^-$ or NO determinations, except that $H_2O_2$ 0.01M -10-5M is included in a trapping mixture intended for NO analysis. Optimally, for NO analysis, the $H_2O_2$ concentration should be about three times the NO concentration. Also, for optimum NO analysis the micellar solution should be acidified, for example, by addition of 2 ml of 0.5% sulfuric acid per 1 l ml. A micelle solution used herein for an NO assay contains 2 $\mu$l of 25% aqueous $H_2O_2$, 2 $\mu$l of 0.5% aqueous $H_2SO_4$, 1 mg CTAB, 1 ml isopropanol, and 10 ml octane. Acidification increases assay sensitivity about 500-fold. The effect of acidification was unexpected in light of Petriconi and Papee (1964) Nature 204:142–144 that indicates that $ONOO^-$ is stable only in alkaline media. In addition, using apparatus of the present invention, the inventors have found that the chemiluminescence signal at neutral pH is very weak, in contrast to results reported by Kikuchi et al. (1993).

The chemiluminescent reagent for $O_2^-$ measurement is prepared by dissolving lucigenin (commercially supplied as the nitrate salt) to $5 \times 10^{-4}$M in normal saline (nominal pH 7.1) together with 0.1M CTAB. The lucigenin-CTAB solution is then mixed with methanol 1:2 (v/v) (lucigenin solution:methanol) to assist lucigenin to enter the emulsion or micelies. The final concentration of lucigenin is $1.67 \times 10^{-4}$M, while CTAB is $3.3 \times 10^{-2}$M. The chemiluminescent reagent solution either breaks the emulsion or enters the emulsion or micelle when mixed with the latter in the mixing cell, allowing the chemiluminescent reaction to occur. Lucigenin reacts specifically with $O_2^-$ to give luminescence, although the details of the reaction remain somewhat uncertain. The light intensity is proportional to the $O_2^-$ concentration. Luminol, for chemiluminescent detection of NO, can be used in the range of $10^{-6}$ to $10^{-5}$M, the optimum concentration being about $5 \times 10^{-6}$M. Luminol is dissolved in 67 mM phosphate buffer at pH 7.4. Since luminol is soluble in the micellar solution there is no need to use alcohol to aid its entry into the micelles containing NO. Luminol reacts with peroxynitrite, $ONOO^-$ to yield intense luminescence proportional to the $ONOO^-$ concentration. Trapped NO is quantitatively converted to $ONOO^-$ by the presence of $H_2O_2$ in the trapping mixture. $H_2O_2$ itself reacts with luminol to yield a weak light emission. However, at the $H_2O_2$ concentrations used herein, the contribution of $H_2O_2$ itself to the luminescence is negligible. A basal level of light emission is observed in the absence of $H_2O_2$. The basal level is believed to be caused by trapped $O_2^-$ in the sample, which also oxidizes NO to $ONOO^-$ [See Radi, R., et al. (1993)]. A further 50-fold increase in signal intensity can be achieved in the NO assay by irradiating the NO trapping mixture with an ultraviolet light source before the mixture contacts the sample. Irradiation of $H_2O_2$ results in formation of radical species including OH which are believed to enhance oxidation of NO to $ONOO^-$ [See Petriconi et al. *Can. J. Chem.* 44:977–980; Petriconi and Papee (1964) supra. Irradiation also reduces or eliminates residual $H_2O_2$ so that the background chemiluminescence is reduced and the effect of any heme in the sample is reduced or eliminated. A shortwavelength ultraviolet lamp such as model UVGL-25, available from Ultraviolet Products, Inc., San Gabriel, Calif., is suitable for use.

Reproducibility can be enhanced, for both $O_2^-$ and NO assays, by incorporating a standard HPLC sample injector valve such as Rheodyne model 7011, available from Rainin, Emeryville, Calif., into the sample flow. The injector has a tubing loop of calibrated volume. Flow of trapped analyte fills the calibrated loop, the injector valve is then positioned to permit the calibrated amount of sample to mix with chemiluminescent reagent and enter the detector while sample flow is shunted to waste. Sample flow from the loop toward the detector is preferably provided by a syringe pump pumping an inert fluid, for example, trapping mixture lacking $H_2O_2$. Sample and chemiluminescent reagent then meet in the mixing cell and proceed to the detector as previously described. The use of the injection valve permits precise sample volume metering and smooth flow through the detector provided by the syringe pump. Sample volumes of 5 μl, 10 μl, 15 μl, 20 μl, 50 μl, etc., are measurable simply by exchanging precalibrated loops. Although depicted separately in the figures, individual syringe pumps, separately controlled, are not required since a single syringe pump can be set up to provide flow for several fluid streams simultaneously, or at selected times, as will be understood in the art.

The discovery that trapping mixtures can be used to sequester $O_2^-$ and/or NO, and to protect them from destructive interactions with aqueous media long enough to carry out a quantitative reaction has opened new avenues for research. For example, trapping could occur as a physiological process. The $O_2^-$ and NO contained within cells can be analyzed directly in an apparatus of the invention with the use of an endogenous trapping mixture. Contact with the hydroalcoholic solution of a chemiluminescent reagent results in cell lysis, reaction of $O_2^-$ or $NO_2$ with the reagent and light emission proportional to the $O_2^-$ or NO trapped in the cells. In this way, the existence of $O_2^-$ trapped in normal, unstressed red blood cells has been detected for the first time.

EXAMPLE 1—Assay for $O_2^-$

Figure 4:
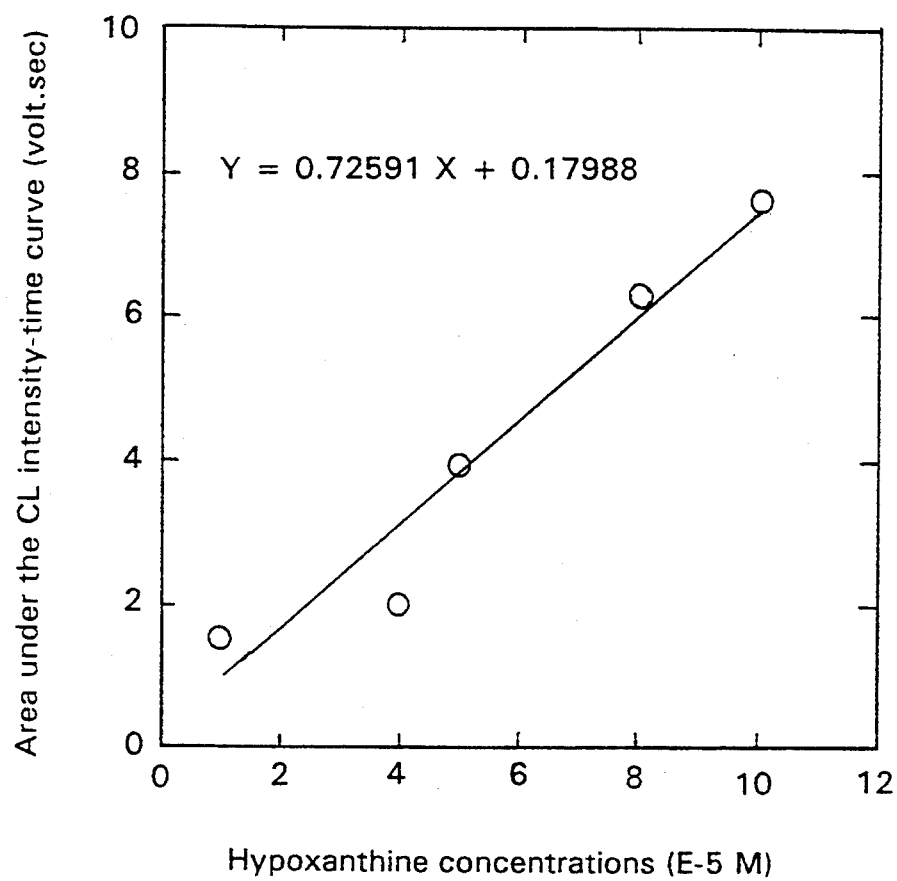
FIG. 4 is a plot of a standard reaction curve showing integrated chemiluminescence light intensity as a function of $O_2^-$ concentration, expressed indirectly as hypoxanthine concentration in a xanthine oxidase/hypoxanthine $O_2^-$ generating reaction.

A standard xanthine oxidase reaction with hypoxanthine as substrate was used to generate $O_2^-$, in a model system to standardize the assay. Each point represents a reaction run to completion giving a light intensity-time curve for a fixed sample volume which was integrated to determine total light yield. The result is shown in FIG. 4. The x-axis shows increasing concentrations of hypoxanthine, from $1 \times 10^{-5}$M to $1 \times 10^{-4}$M. At a maximum, each mole of hypoxanthine oxidized results in 2 moles $O_2^-$ produced. However, the actual amount of hypoxanthine oxidized is less than the maximum theoretical amount, perhaps as low as 28% [Ohara et al. (1993), *J. Clin. Invest.* 91:2546–2551]. The y-axis of FIG. 4 is the area under the light-intensity-time curve, in units of volt seconds for each reaction. A relationship represented by Y-0.72591X+0.17988 fit the data with a correlation coefficient of 0.99. Under the conditions used, with a sample cell volume of 40 μl, the limit of detection was estimated about 20 pmol. The assay was validated by quenching the luminescence signal by addition of superoxide dismutase.

EXAMPLE 2—Assay for NO

Figure 5:
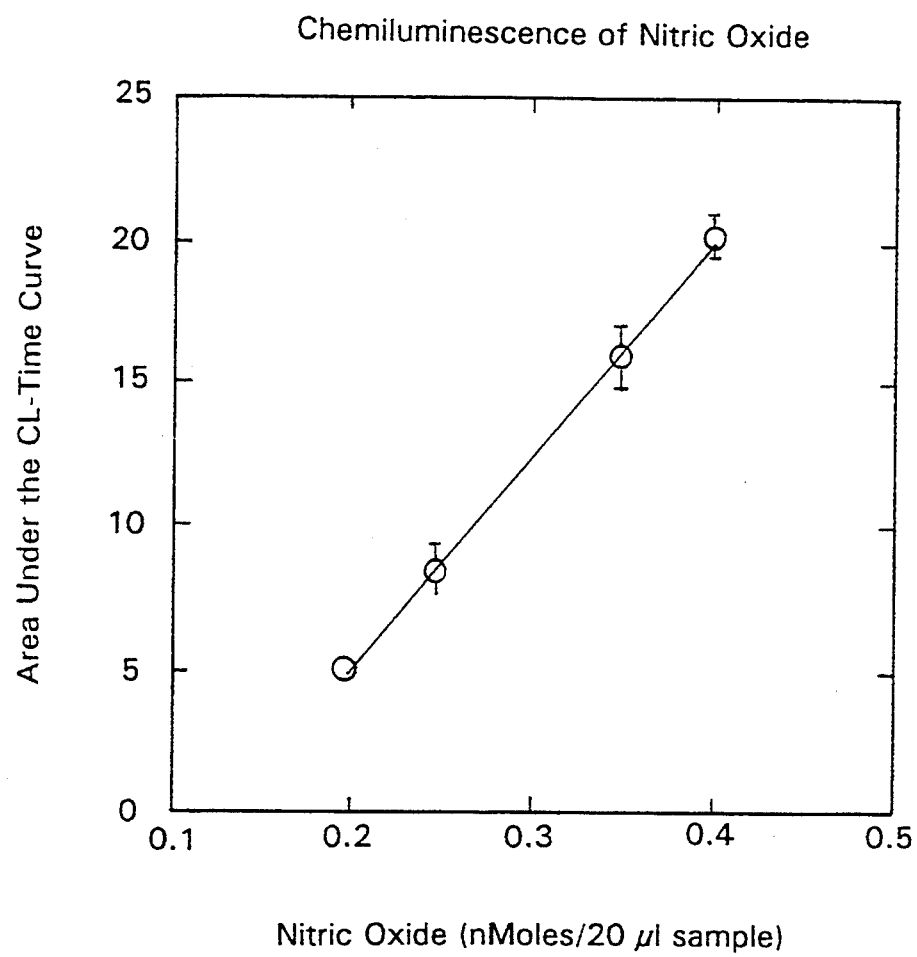
FIG. 5 is a plot of a standard reaction curve for a NO assay showing integrated chemiluminescence light intensity as a function of NO concentration.

A sample containing NO was prepared by bubbling a 1% NO, 99% $N_2$ gas mixture through the sample, together with varied proportions of additional pure $N_2$ to equilibrate the sample to the desired NO concentration. Chemiluminescent light was measured for a fixed sample volume and integrated as described for Example 1. Results are shown in FIG. 5. The relationship Y-75.298X+10.324 fit the data with a correlation coefficient of 0.999. The assay was validated by bubbling $O_2$ into the sample, which obliterated the chemiluminescence signal. $O_2$ reacts with NO to produce nitrate and nitrite. Attempts to validate the assay by UV absorption were unsuccessful because solutions of $ONOO^-$ (produced by NO and $H_2O_2$), $HNO_3$, $NaNO_3$, and $NaNO_2$ all had essentially the same UV spectrum with a broad diffuse band centered at 290 nm-305 μm. Given the conditions of the assay and a 20 μl sample size, the limit of detection was calculated as about 0.2 nmol.

The present invention is not limited by the specific embodiments and examples disclosed herein. Those skilled in the art can and will recognize alternative expedients for carrying out the claimed invention based upon knowledge available to the art. For example, alternative trapping mixtures, analytical reagents and detectors are contemplated as equivalent means for carrying out the invention. Alternative sampling means and strategies for rapidly sequestering $O_2^-$ or NO in a trapping medium are also contemplated as equivalent aspects of the invention as disclosed and claimed herein. Variations of flow parameters, stopped flow and batchwise analysis are also equivalents known to those of ordinary skill in the art.

We claim:

1. A method for assaying $O_2^-$ or NO in an aqueous medium sample comprising the steps of contacting the $O_2^-$ or NO containing sample with a trapping mixture comprising a nonaqueous, aprotic solvent dispersed as an emulsion or micellar suspension whereby the $O_2^-$ or NO is trapped in the solvent, reacting the trapped $O_2^-$ or NO with an analytical reagent capable of yielding a measurable response caused by reaction of the reagent with $O_2^-$ or with NO, said response having a quantity that is a function of the amount of $O_2^-$ or NO, and measuring the quantity of response caused by reaction of the reagent with $O_2^-$ or NO, whereby the $O_2^-$ or NO in the sample is assayed.

2. The method of claim 1, wherein the analytical reagent is a chemiluminescent compound and the response caused by reaction with $O_2^-$ or NO is light emission.

3. The method of claim 2, adapted for $O_2^-$, wherein the analytical reagent is lucigenin dissolved in a hydroalcoholic solution.

4. The method of claim 2, adapted for NO, wherein the analytical reagent comprises luminol and $H_2O_2$.

5. The method of claim 4 wherein the reagent is acidified.

6. The method of claim 4 wherein the trapping mixture is irradiated with ultraviolet light before contacting the sample.

7. The method of claim 1 wherein the trapping mixture is a micellar suspension comprising a cationic detergent.

8. Apparatus for assaying $O_2^-$ or NO in an aqueous sample comprising a sample probe, a mixing cell and a detection cell connected by fluid flow conducting means such that sample entering the sample probe flows thence to the mixing cell and thence to the detection cell, and further comprising trapping mixture pumping means, analytical reagent pumping means, net flow generating means and detection means, the trapping mixture pumping means being connected by fluid flow conducting means to the sample probe for pumping a trapping mixture to the sample probe where $O_2^-$ or NO of a sample is trapped in the trapping mixture, the analytical reagent pumping means being connected by fluid flow conduction means to the mixing cell, the net flow generating means being positioned and regulated to provide net fluid flow in a direction from the sample toward the detection cell, the detector being positioned adjacent the detection cell such that a signal generated within the detection cell is measurable by the detector.

9. Apparatus of claim 8 wherein the detector is a photon counter for measuring chemiluminescence.

10. Apparatus of claim 8 wherein the sample probe comprises an inner micropipette coaxially positioned within an outer micropipette, both inner and outer micropipettes having openings within the sample probe and proximal to the sample, the opening of the inner micropipette being recessed relative to the opening of the outer micropipette, the outer micropipette being connected by fluid flow conduction means to the trapping mixture pumping means, the inner micropipette being connected by fluid flow conduction means to the mixing cell.

11. Apparatus of claim 8 wherein the trapping mixture pumping means and analytical reagent pumping means are syringe pumps.

12. Apparatus of claim 10 wherein the trapping mixture pumping means and net flow generating means are regulatable such that the rate of trapping mixture flow through the outer micropipette is less than the rate of fluid flow through the inner micropipette.

13. Apparatus of claim 8 wherein the analytical reagent pumping means comprises two analytical reagent reservoirs and means for alternatively switching flow of analytical reagent from either a first analytical reagent reservoir or a second analytical reagent reservoir toward the mixing cell.

14. Apparatus of claim 8 wherein the trapping mixture pumping means comprises means for mixing together two components of the trapping mixture.

15. Apparatus of claim 8 further comprising an ultraviolet light irradiation source positioned to irradiate the trapping mixture between the trapping mixture pumping means and the sample probe.

* * * * *